United States Patent [19]

Ruf

[11] Patent Number: 5,087,711
[45] Date of Patent: Feb. 11, 1992

[54] METHOD FOR THE PREPARATION OF TETRAALKYL-TIN

[75] Inventor: Erich Ruf, Essen-Haarzopf, Fed. Rep. of Germany

[73] Assignee: Th. Goldschmidt AG, Essen, Fed. Rep. of Germany

[21] Appl. No.: 648,572

[22] Filed: Jan. 31, 1991

[30] Foreign Application Priority Data

Feb. 26, 1990 [DE] Fed. Rep. of Germany ........ 4006043

[51] Int. Cl.$^5$ .............................. C07F 7/22; C07F 7/30
[52] U.S. Cl. ..................................... 556/102; 556/90; 556/95
[58] Field of Search ........................... 556/90.95, 102

[56] References Cited

U.S. PATENT DOCUMENTS

| | | | |
|---|---|---|---|
| 3,027,393 | 3/1962 | Jenkner et al. | 260/429.7 |
| 3,059,012 | 10/1962 | Hechenbleikner et al. | 260/429.7 |
| 3,103,526 | 9/1963 | Jenkner | 260/431 |
| 3,211,769 | 10/1965 | Brown et al. | 260/429.7 |

FOREIGN PATENT DOCUMENTS

| | | | |
|---|---|---|---|
| 0242270 | 12/1962 | Australia | 556/102 |
| 0802796 | 10/1958 | United Kingdom | 556/102 |

*Primary Examiner*—Jose G. Dees
*Assistant Examiner*—Porfirio Nazario
*Attorney, Agent, or Firm*—Toren, McGeady & Associates

[57] ABSTRACT

A method is disclosed for the preparation of tetraalkyltin wherein tin-tetraacetate is first dispersed in tetrahydrofuran and trialkyl-aluminum is slowly added to the dispersion in an amount sufficient to cause complete reaction. The reaction is carried out at a temperature of <80° C. The reaction mixture is then heated to the reflux temperature of the tetrahydrofuran for about 1 to 2 hours and until complete reaction. The aluminum triacetate is then removed and the tetrahydrofuran is distilled off.

2 Claims, No Drawings

METHOD FOR THE PREPARATION OF TETRAALKYL-TIN

FIELD OF INVENTION

The invention generally is directed to organic tin compounds and is particularly concerned with a method for the preparation of tetraalkyl-tin whose alkyl groups each have 1 to 18 carbon atoms, preferably 1 to 8 carbon atoms.

BACKGROUND INFORMATION AND PRIOR ART

It is known that tetraalkyl-tin is obtained by the reaction of tin-(IV)-chloride with trialkyl-aluminum. In order to obtain a high yield, the reaction has to be performed under relatively high reaction temperatures of >80° C., particularly temperatures of about 200° C.

A considerable disadvantage of this reaction is that the aluminum chloride which is formed in the reaction forms complex salts with dialkyl-tin-dichloride and trialkyl-tin-monochloride, to wit: compounds which are formed during the reaction as intermediate compounds. The formation of these complexes prevents further alkylation of the compounds to form tetraalkyl-tin. The reaction, therefore, has to be carried out in the presence of suitable complex forming agents for the aluminum-trichloride. Ether, sodium chloride or tertiary amines are used as such complex forming agents.

The alkylation in the presence of ether takes place according to the following reaction scheme:

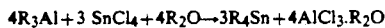

$$4R_3Al + 3 SnCl_4 + 4R_2O \rightarrow 3R_4Sn + 4AlCl_3 \cdot R_2O$$

wherein R=alkyl.

OBJECTS OF THE INVENTION

It is the primary object of the invention to provide a method which enables the production of tetraalkyl-tin under favorable conditions and with good yield, and which can be carried out in a simple manner with readily accessible starting materials.

It is another object of the invention to provide a method of the indicated kind which eliminates the use of complex forming agents.

Generally, it is an object of the invention to improve on the art of preparing tetraalkyl-tin.

SUMMARY OF THE INVENTION

Pursuant to the invention, tetraalkyl-tin is prepared by the combination of the following method steps:
(a) dispersing tin-tetraacetate in tetrahydrofuran;
(b) adding trialkyl-aluminum to the dispersion, the alkyl groups having 1 to 18 carbon atoms; the trialkyl-aluminum is added very slowly and in an amount necessary for the complete reaction with the tin-tetraacetate. This amount has to be at least stoichiometric;
  (b1) the addition of the trialkyl-aluminum to the dispersion is carried out under controlled temperature conditions so that a temperature in the reaction mixture of <80° C. is maintained;
(c) heating the reaction mixture to the reflux temperature of the tetrahydrofuran during a time period of about 1 to 2 hours until complete reaction has taken place; and
(d) separating the formed aluminum triacetate and removing the tetrahydrofuran by distillation.

Method step (a), to wit, dispersing the tin-tetra-acetate and tetrahydrofuran is performed under stirring.

Method step (b) takes place under heat generation since the reaction is exothermic. The addition of trialkyl-aluminum should therefore be effected very slowly since the temperature of the reaction mixture is not permitted to exceed 80° C. Preferably, the reaction should take place at a temperature <65° C. The reaction mixture therefore has to be cooled, as a rule, in order to dissipate the reaction heat rapidly.

The amount of the trialkyl-aluminum to be added corresponds to the stoichiometrically required amounts. In other words, for the reaction of 1 mole of tin-tetraacetate, about 1.3 to 1.4 moles of trialkyl-aluminum are required. It is advantageous if an excess above the stoichiometrically required amount of trialkyl-aluminum is added in step (b). An excess of up to about 10% is suitable. Particularly preferred is an excess of about 5% above the stoichiometrically required quantity.

After the trialkyl-aluminum has been added, the reaction temperature in method step (c) is slightly raised and the reaction mixture is heated under reflux for about 1 to 2 hours. The anhydrous aluminum triacetate formed in the reaction is, from a practical point of view, insoluble in the tetrahydrofuran and precipitates.

The precipitated aluminum triacetate is separated in method step (d). The separation is advantageously accomplished by filtration. The tetrafuran is removed from the filtrate by distillation, preferably at reduced pressure. The desired tetraalkyl-tin is obtained in pure form.

The anhydrous aluminum triacetate obtained in the inventive procedure is a valuable compound which has several uses. Thus, it is an excellent catalyst in esterification, reesterification and condensation reactions and particularly poly-condensation reactions.

The invention will now be described by two examples, it being understood that these examples are given by way of illustration and not by way of limitation.

EXAMPLE 1

This experiment was carried out in a 250 ml four neck flask fitted with a stirrer, drop funnel, cooler with argon supply and thermometer. 71 gram of tin-tetraacetate and 106.5 gram of tetrahydrofuran are added to the flask. While stirring and passing argon through the reaction apparatus, 102.7 gram of trioctyl-aluminum are slowly added to the slurry of tin-tetraacetate and tin-tetrahydrofuran in dropwise manner. The drop addition lasted for 1 hour and 40 minutes.

The reaction mixture is cooled in such a manner that the temperature is <65° C. After the entire amount of trioctyl-aluminum has been added, the reaction mixture is heated for 1 to 2 hours to the reflux temperature of tetrahydrofuran while stirring. Thereafter, the precipitated aluminum tri-acetate is removed by filtration through a sintered glass filter device capable of connection to a vacuum source and is washed three times each with 100 ml tetrahydrofuran. The product is dried in vacuum (about 1 mm Hg) at room temperature and the yield ws 55.2 gram of aluminum triacetate.

The filtrate, as well as the tetrahydrofuran amount used for the washing of the aluminum triacetate, were combined and then tetrahydrofuran was removed by distillation in a water jet vacuum (about 15 mm Hg).

105.9 gram of clear, colorless tetraoctyl-tin are obtained.

EXAMPLE 2

In a manner analogous to that described in Example 1, 71 gram tin-tetraacetate are reacted in 106.5 gram of tetrahydrofuran with 55.5 gram of tributyl-aluminum. The processing is done as in Example 1.

53.7 gram of aluminum triacetate and 65.1 gram of tetrabutyl-tin are obtained. The yield of tetrabutyl-tin is calculated on the product amount obtained after vacuum distillation (about 1 mm Hg).

I claim:

1. A method for the production of tetraalkyl-tin, wherein the alkyl groups each contain 1 to 18 carbon atoms, comprising:
    (a) dispersing tin-tetraacetate in tetrahydrofuran;
    (b) slowly adding to the dispersion trialkyl-aluminum whose alkyl groups each contain 1 to 18 carbon atoms, the amount of said trialkyl-aluminum being sufficient for complete reaction with the tin-tetraacetate and being at least a stoichiometric amount;
    (b1) conducting step (b) in such a manner that the temperature in the reaction mixture is $<80°$ C.;
    (c) heating the reaction mixture to the reflux temperature of the tetrahydrofuran in the mixture during a time period of about between 1 to 2 hours and until complete reaction; and
    (d) separating the aluminum tri-acetate formed and removing the tetrahydrofuran by distillation.

2. A method as claimed in claim 1, wherein the amount of trialkyl-aluminum added in step (b) is in excess to the stoichiometric amount, said excess being up to about 10%.

* * * * *